United States Patent [19]

Zinnen

[11] Patent Number: 5,149,887
[45] Date of Patent: Sep. 22, 1992

[54] SEPARATION OF ALKYL-SUBSTITUTED PHENOLIC ISOMERS WITH BARIUM-POTASSIUM EXCHANGED ZEOLITIC ADSORBENT

[75] Inventor: Hermann A. Zinnen, Summit, N.J.

[73] Assignee: UOP, Des Plaines, Ill.

[21] Appl. No.: 624,810

[22] Filed: Dec. 10, 1990

Related U.S. Application Data

[63] Continuation-in-part of Ser. No. 458,256, Dec. 28, 1989, abandoned.

[51] Int. Cl.$^5$ ........................ C07C 37/82; C07C 37/70
[52] U.S. Cl. .................................... 568/751; 568/750; 568/752
[58] Field of Search ........................ 568/750, 751, 752

[56] References Cited

U.S. PATENT DOCUMENTS 4,124,770  11/1978  Miyakes et al. ............... 568/758
4,356,331  10/1982  Inoune ........................... 568/758
4,386,225   5/1983  Neuzil ............................ 568/751

FOREIGN PATENT DOCUMENTS 0045432  4/1981  Japan ........................... 568/758

Primary Examiner—Werren B. Lone
Attorney, Agent, or Firm—Thomas K. McBride; John F. Spears, Jr.; Jack H. Hall

[57] ABSTRACT

A process for the coextraction of para-cresol and meta-cresol from a feed mixture comprising p-cresol, o-cresol and m-cresol and one other alkyl phenol with an adsorbent comprising an X zeolite exchanged with barium ions or a mixture of barium and potassium ions at exchangeable sites to preferentially adsorb both para- and meta-cresol. The adsorbent must contain at least about 5 wt. % water (LOI method). The coextracted cresol isomers are thereafter removed from the adsorbent by contacting it with a desorbent material and recovering said coextracted cresols as a product stream. Para-cresol and meta-cresol can thereafter be recovered as purified individual isomers by a second state adsorptive separation using a second adsorbent selective for para-cresol, e.g., said first adsorbent dried to an LOI of less than about 4 wt. %, preferably about 2 wt. % water. In a preferred embodiment, the process uses a simulated moving-bed countercurrent flow system in both adsorption separation steps.

6 Claims, 2 Drawing Sheets

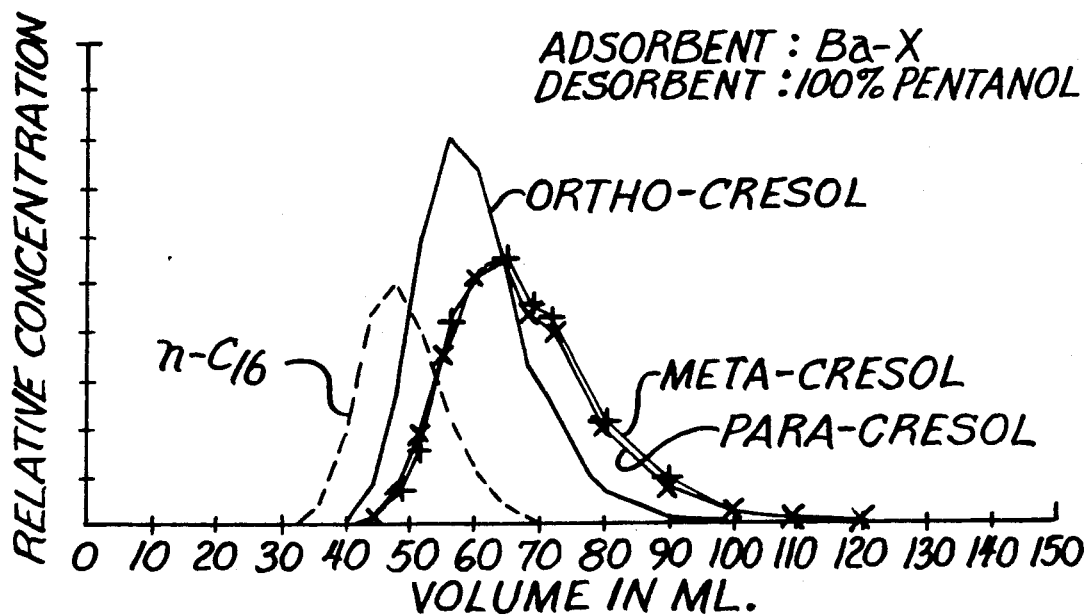
FIG. 3
FIG. 4
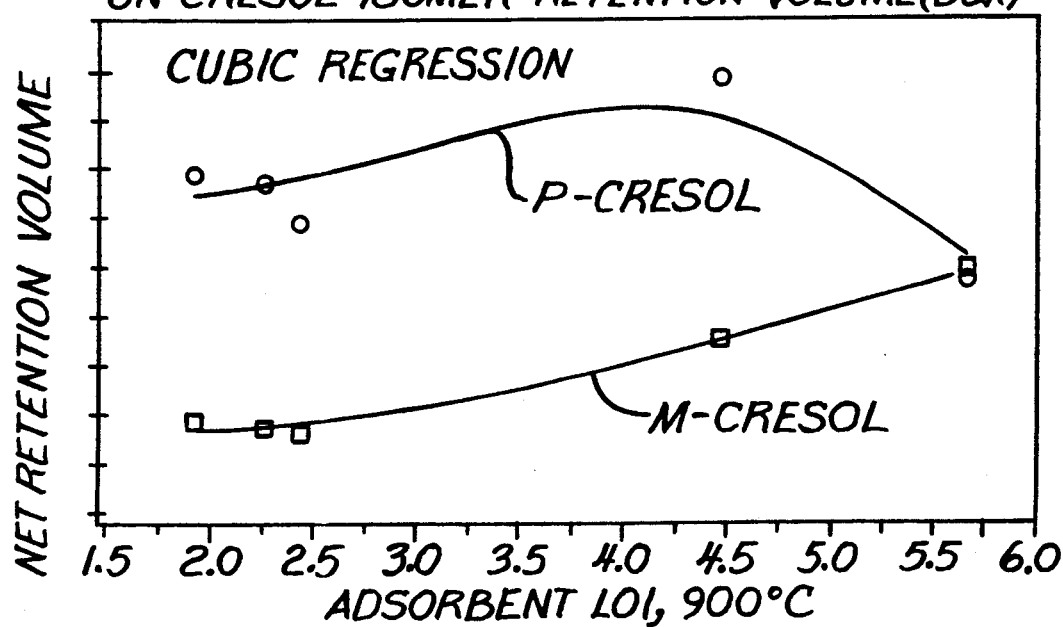

SEPARATION OF ALKYL-SUBSTITUTED PHENOLIC ISOMERS WITH BARIUM-POTASSIUM EXCHANGED ZEOLITIC ADSORBENT

CROSS-REFERENCE TO RELATED APPLICATION

This application is a continuation in-part of U.S.S.N. 458,256 filed Dec. 28, 1989, abandoned.

FIELD OF THE INVENTION

The field of art to which the claimed invention pertains is the separation of phenolic isomers. More specifically, the invention relates to a process for coextracting the para- and meta-cresol isomers from a feed mixture comprising ortho-, meta- and para-cresol and at least one other alkyl phenol with a particular zeolitic adsorbent. This invention employs a particular flow scheme to subsequently separately recover the para- and meta-isomers from the feed.

BACKGROUND OF THE INVENTION

The cresol isomers are in substantial demand for various applications in the manufacture of phenolic resins, plasticizers, inhibitors, agricultural chemicals, ore flotation chemicals, germicides, antiseptics and disinfectants. The use varies with the particular isomer. For example, para-cresol is particularly useful in disinfectants or fumigating compositions, in production of cresotimic acid, dye stuffs and organic intermediates.

Meta-cresol is particularly useful as a disinfectant, fumigating compositions, photographic chemicals, ore flotation chemicals, paint and varnish removers, in the production of synthetic resins, explosives and organic chemicals.

Furthermore, applications for intermediates or final products utilizing a purified mixture of para- and meta-cresol exist, especially in the commercially important butylation of mixed m- and p-cresols. Previous adsorptive separation processes were suitable for extracting the para-cresol isomer from meta- and ortho-cresol, but effective processes for separating both para- and meta-cresol were not available.

Adsorptive processes for separating cresol isomers have been previously known, e.g., from U.S. Pat. Nos. 3,014,078; 3,969,422 and 4,356,331. Also the separation of xylenols from cresols with adsorbents is known, for example, from U.S. Pat. Nos. 4,124,770 and 4,386,225.

More specifically, U.S. Pat. No. 3,014,078 teaches the separation of cresol isomers by employing an adsorbent consisting of an X-type zeolite exchanged with calcium, barium, etc., to selectively adsorb cresol from a cresol isomer feed mixture thereby producing a rich adsorbent. In the preferred mode of operation, the adsorbed isomer is then removed by contacting with a displacement exchange fluid. A preferred displacement exchange fluid is phenol although other materials which may be employed include ethers, aromatic hydrocarbons, and paraffin hydrocarbons.

U.S. Pat. No. 4,356,331 discloses a process for selectively adsorbing an alkyl phenol isomer onto a potassium exchanged Y zeolite, preferably also containing an additional cation, e.g., strontium or barium and subsequently desorbing the selectively adsorbed isomer with an aliphatic ketone desorbent. This patent disclosure is directed specifically to the separation of p-cresol from m-cresol and contains no suggestion of applicant's separation.

U.S. Pat. No. 3,969,422 to Neuzil et al discloses a process for separating para-cresol from at least one other cresol isomer, especially meta-cresol, with the preferred adsorbent being barium-potassium exchanged X zeolite and the preferred desorbent being a saturated alcohol from 1 to 7 carbon atoms per molecule. Likewise, there is no disclosure of applicant's co-extraction of meta- and para-cresol from mixtures of ortho-cresol and other alkyl phenols.

The separation of xylenols from cresols with X or Y zeolites exchanged with various cations or mixtures thereof, e.g., potassium and barium, and alcohols as desorbents was discused in Neuzil Patent 4,386,225 and U.S. Pat. No. 4,124,770. In both patents containing similar disclosures all cresol isomers are extracted to substantially exclude the xylenol, which is collected in the raffinate. No disclosure of the critical role of water in the invention is contained in either patent.

The present invention relates to an improved process for separating the cresol isomers, by which high purity products of both para-cresol and meta-cresol can be obtained. In particular, we have found that by employing a particular adsorbent material, a co-extract of meta- and para-cresol can be obtained which can be subsequently separated into pure fractions of the individual isomers, meta-cresol and para-cresol, e.g., by a second stage adsorption process utilizing the same adsorbent and desorbent. Both products are valuable and therefore the ability to obtain highly pure fractions of each of the isomers of cresol is desirable.

It is also known that crystalline aluminosilicates or zeolites are used in adsorption separations of various mixtures in the form of agglomerates having high physical strength and attrition resistance. Methods for forming the crystalline powders into such agglomerates include the addition of an inorganic binder, generally a clay comprising a silicon dioxide and aluminum oxide, to the high purity zeolite powder in wet mixture. The blended clay zeolite mixture is extruded into cylindrical type pellets or formed into beads which are subsequently calcined in order to convert the clay to an amorphous binder of considerable mechanical strength. As binders, clay of the kaolin type or silica are generally used.

The invention herein can be practiced in fixed or moving adsorbent bed systems or in cocurrent, pulsed batch systems described in U.S. Pat. No. 4,159,284 or in cocurrent continuous simulated moving bed systems like that disclosed in Gerhold Patents 4,402,832 and 4,478,721, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRosset U.S. Pat. No. 3,706,812) to commercial scale in flow rates from a few cc per hour to many thousands of gallons per hour.

The functions and properties of adsorbents and desorbents in the chromatographic separation of liquid components are well known, but for reference thereto, Zinnen et al U.S. Pat. No. 4,642,397 is incorporated herein.

SUMMARY OF THE INVENTION

In brief summary, the present invention is a process for coextracting the para- and meta-cresol isomers from a feed mixture comprising para-, ortho- and meta-cresol and at least one other alkyl phenol, which process comprises contacting, at adsorption conditions, the feed mixture with an adsorbent comprising an X type zeolite exchanged at ion exchangeable sites with barium ions or a mixture of barium and potassium ions, containing at least about 5 weight % water (LOI method) to effect the selective adsorption of both the para-isomers and meta-cresol isomers and thereafter recovering the para- and meta-cresol isomers by contacting said adsorbent, containing the selectively adsorbed isomers, with a desorbent, at desorption conditions. The desorbent may be an aliphatic alcohol and $C_5$ and $C_6$ aliphatic alcohols are preferred. In a subsequent step para-cresol can be separated from the meta-cresol by further contacting the same adsorbent, having less than about 4 wt.% and preferably about 2 wt.% water (LOI method), with the extract from the first stage (after removing most of the desorbent by flashing) and desorbing the para-cresol at desorption conditions with a desorbent, which may be the same as in the first step.

Other embodiments of the present invention encompass details about feed mixtures, adsorbent, desorbent materials, flow schemes and operating conditions all of which are hereinafter disclosed in the following discussion of each of the facets of the present invention.

BRIEF DESCRIPTION OF THE DRAWINGS

FIG. 3 is similar to FIG. 1, except that the adsorbent was Ba-X having a water content (LOI) of 5.66%.

FIG. 4 is a summary of the pulse test data of Example II, using Ba-X, in which net retention volume (NRV) is plotted vs. water content (LOI).

DESCRIPTION OF THE INVENTION

Figure 1:
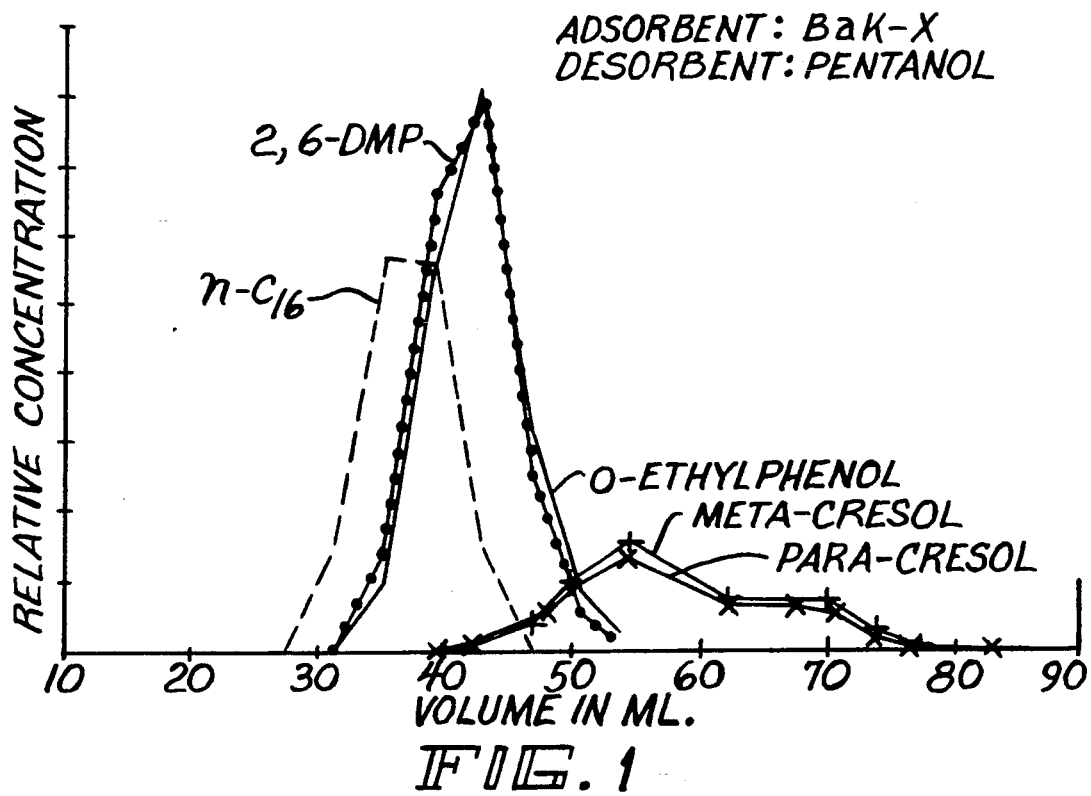
FIG. 1 is a chromatographic separation (pulse test) of a feed mixture containing m- and p-cresol, 2,6-dimethyl phenol and o-ethyl phenol with a Ba/K-X zeolite containing 5.48% water (LOI) and n-pentanol as the desorbent.

Adsorbents to be used in the process of this invention comprise specific crystalline aluminosilicates or molecular sieves, namely X zeolites, exchanged at exchangeable cationic sites with barium and potassium ions. The zeolites have known cage structures in which the alumina and silica tetrahedra are intimately connected in an open three-dimensional network to form cage-like structures with window-like pores. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves", although widely used, is not strictly suitable since the separation of specific aromatic isomers is apparently dependent on differences in electrochemical attraction of the different isomers and the adsorbent rather than on pure physical size differences in the isomer molecules.

In hydrated or partially hydrated form the preferred type X crystalline aluminosilicates encompass those zeolites represented, in terms of moles of metal oxides, by the formula 1 below:

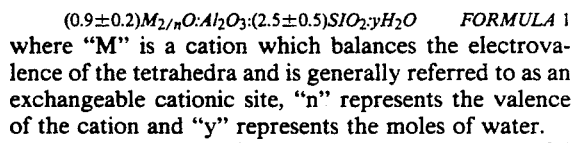

$$(0.9\pm0.2)M_{2/n}O:Al_2O_3:(2.5\pm0.5)SiO_2:yH_2O \quad \text{FORMULA 1}$$

where "M" is a cation which balances the electrovalence of the tetrahedra and is generally referred to as an exchangeable cationic site, "n" represents the valence of the cation and "y" represents the moles of water.

Adsorbents comprising the type X zeolites are useful for the adsorptive process for co-extracting m- and p-cresol from mixtures of alkyl phenols herein described. These zeolites are described and defined in U.S. Pat. No. 2,882,244. The term "type X structured" zeolites as used herein shall include all zeolites which have general structures as represented in the above cited patent.

Typically, the type X structured zeolites, as initially prepared, are predominantly in the sodium form. The term "exchanged cationic site" generally refers to the site in the zeolite occupied by the cation "M". This cation, usually sodium, can be replaced or exchanged with other specific cations, dependent on the type of the zeolite to modify characteristics of the zeolite. The preferred zeolites for use in this invention are type X zeolites exchanged with barium ions or a mixture of barium and potassium ions.

Cations occupying exchangeable cationic sites in the zeolite are exchanged with other cations by ion exchange methods well known to those having ordinary skill in the field of crystalline aluminosilicates. Such methods are generally performed by contacting the zeolite or an adsorbent material containing the zeolite with an aqueous solution of the soluble salt of the cation or cations desired to be placed upon the zeolite. After the desired degree of exchange takes place, the sieves are removed from the aqueous solution, washed, then dried to a desired water content. By such methods, the sodium cations and any non-sodium cations which might be occupying exchangeable sites as impurities in a sodium-X zeolite can be essentially completely replaced with other cations. It is preferred that the zeolite used in the process of this invention contain barium or a combination of barium and potassium cations at exchangeable cationic sites prepared as disclosed in the above mentioned U.S. Pat. No. 3,969,422. The weight ratio of barium oxide to potassium oxide in one of the preferred adsorbents can be from about 15.9 to about 6.5.

It has been found that an adsorbent comprising an X zeolite containing at exchangeable cationic sites barium cations or a mixture of barium and potassium cations satisfies the selectivity requirements and other adsorbent requirements previously discussed and are therefore preferred for use in this process. Adsorbents for this process may be prepared by partially (for mixed cations) or essentially completely ion exchanging potassium-type X base material, in a particle size range of from about 20 to about 40 U.S. Mesh, with barium cations. Typically the ion exchanges will be done with aqueous solutions of the soluble salts, such as the chlorides, of the respective metal. The term "essentially complete" shall mean that the residual potassium content of the adsorbent after the ion exchange of the base material shall be less than about 2 wt.% $K_2O$. After ion-exchange and water wash to remove excess ion exchange solution, the adsorbent will be dried to reduce the water content as measured by loss on ignition (LOI) at 900° C. to not less than about 5 wt.% and more preferably within a range of from about 5 to about 7 wt.%, and most preferably about 5.5 to 6 wt.% (LOI). Maintaining adsorbent water content above about 5% is critical to process performance and water may be added to the process during operations as necessary to maintain this minimum level. Water may be added to the adsorbent, if necessary, either on an intermittent or more preferably on a continuous basis by itself or in admixture with feed or desorbent material to maintain the desired concentration of water on the adsorbent.

Typically, adsorbents used in separative processes contain the crystalline material dispersed in an amorphous inorganic matrix or binder, having channels and cavities therein which enable liquid access to the crystalline material. Amorphous material such as silica, or silica-alumina mixtures or compounds, such as clays, are typical of such inorganic matrix materials. The binder aids in forming or agglomerating the crystalline particles of the zeolite which otherwise would comprise a fine powder. The adsorbent may thus be in the form of particles such as extrudates, aggregates, tablets, macrospheres or granules having a desired particle size range, from about 16 to about 40 mesh (Standard U.S. Mesh) (1.9 MM to 250 $\mu$).

Feed mixtures which can be used in the process of the invention include complex mixtures of cresol isomers and other alkyl phenols, obtained from coal tar, coal gasification, or synthetic processes, including p-cresol, m-cresol, o-cresol, m-ethyl phenol, o-ethyl phenol, p-ethyl phenol, dimethyl phenols, diethyl phenols, methyl ethyl phenols and isopropyl phenols. A typical feed derived from coal tar was analyzed as follows:

TABLE 1

| Component | Wt. % |
| --- | --- |
| m-Cresol | 50 |
| p-Cresol | 45.3 |
| 2,6 Dimethyl Phenol (DMP) | 1.0 |
| o-Ethyl Phenol | 3.0 |
| o-Cresol | 0.4 |
| 2,4 + 2,5 DMP | 0.3 |
| | 100.00 |

In the preferred isothermal, isobaric, liquid-phase operation of the process of my invention, I have found that desorbent materials comprising aliphatic alcohols ($C_5$–$C_6$), selected to differ in boiling point by at least 5° C. from the boiling range of the feedstock so the desorbent may be recovered for reuse, will result in selectivity for the coextracted product when used with the above discussed adsorbent.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 20° to about 200° C. and a pressure sufficient to maintain liquid phase, ranging from about atmospheric to about 500 psig. Desorption conditions will include the same range of temperatures and pressures as used for adsorption conditions.

At least a portion of the extract stream, and preferably at least a portion of the raffinate stream, from the separation process, are passed to separation means, typically fractionators or evaporators, where at least a portion of the desorbent material is separated to produce a co-extract product and a raffinate product, respectively. The raffinate will contain the less strongly adsorbed components of the feed, e.g., o-cresol, the dimethyl phenols, the ethyl phenols, etc.

The coextract product taken from the first stage contains a highly purified mixture of para-cresol and meta-cresol. These two components may be separated in a second stage adsorptive separation, similar to the first, in which an adsorbent selection for para-cresol is used. Part or all of the desorbent from the first stage may be removed from the first extract, but if the same desorbent is used in the second stage, some of the desorbent from the first stage will not be detrimental if left in the feed to the second stage. The adsorbent may be any para-selective adsorbent, such as disclosed in U.S. Pat. No. 4,356,331 or Neuzil et al 3,969,422, but it is preferred to use the same adsorbent as the first stage, but having a water content below about 4% (wt.) whereby the adsorbent is selective for para-cresol. The desorbent may be selected from the desorbents disclosed in said patents, e.g. an aliphatic alcohol or a mixture thereof with an aliphatic ketone, but it is preferred to use the same desorbent as the first stage.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of the feed mixture is injected for a duration of several minutes. Desorbent flow is resumed, and the m- and p-cresol coextract and other components are eluted as in a liquid-solid chromatographic operation. The effluent can be analyzed on stream or alternatively, effluent samples can be collected periodically and later analyzed separately by analytical equipment and traces of the envelopes of corresponding component peaks developed.

From information derived from the test, adsorbent performance can be rated in terms of void volume, retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, ($\beta$), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

The following examples are presented to illustrate the selectivity relationship that makes the process of this invention possible. The examples are not intended to unduly restrict the scope the claims.

EXAMPLE I

The purpose of this example is to present the results of a pulse test obtained from the above described pulse test apparatus packed with barium and potassium exchanged X (BaK) zeolite with 1-pentanol desorbent to separate and recover para-cresol and meta-cresol from a feed mixture of 0.3 g of 2,6-dimethyl phenol (DMP), 0.3 cc each of o-ethyl phenol, m-cresol, p-cresol, 0.25 cc n-$C_{16}$ (tracer) and 2.0 cc 1-pentanol (desorbent).

A feed pulse consisting of 2.0 cc of the above mixture was introduced to the pulse test column at 135° C. The desorbent flow rate was 1.17 cc/min. The water content of the adsorbent was 5.48% (LOI at 900° C.).

From the plot of relative concentration (by gas chromatographic area counts) vs. net retention volume (NRV) in ml. shown in FIG. 1, selectivities calculated among the various compounds are set forth in the following Table 2 (under the headings gross retention volume, net retention volume and selectivity factor ($\beta$) of each component with respect to the reference component, p-cresol):

TABLE 2

| Component | Gross Retention Volume | Net Retention Volume | Peak Width At Half Height | Selectivity Factor $\beta$ |
|---|---|---|---|---|
| n-$C_{16}$ | 37 | 0 | 9.2 | Tracer |
| 2,6-DMP | 41.4 | 4.40 | 8.6 | 4.18 |
| o-Ethyl Phenol | 41.8 | 4.8 | 8.4 | 3.83 |
| p-Cresol | 55.4 | 18.4 | 13.7 | Refer. |
| m-Cresol | 55.3 | 18.3 | 13.1 | 1.005 |

Figure 2:
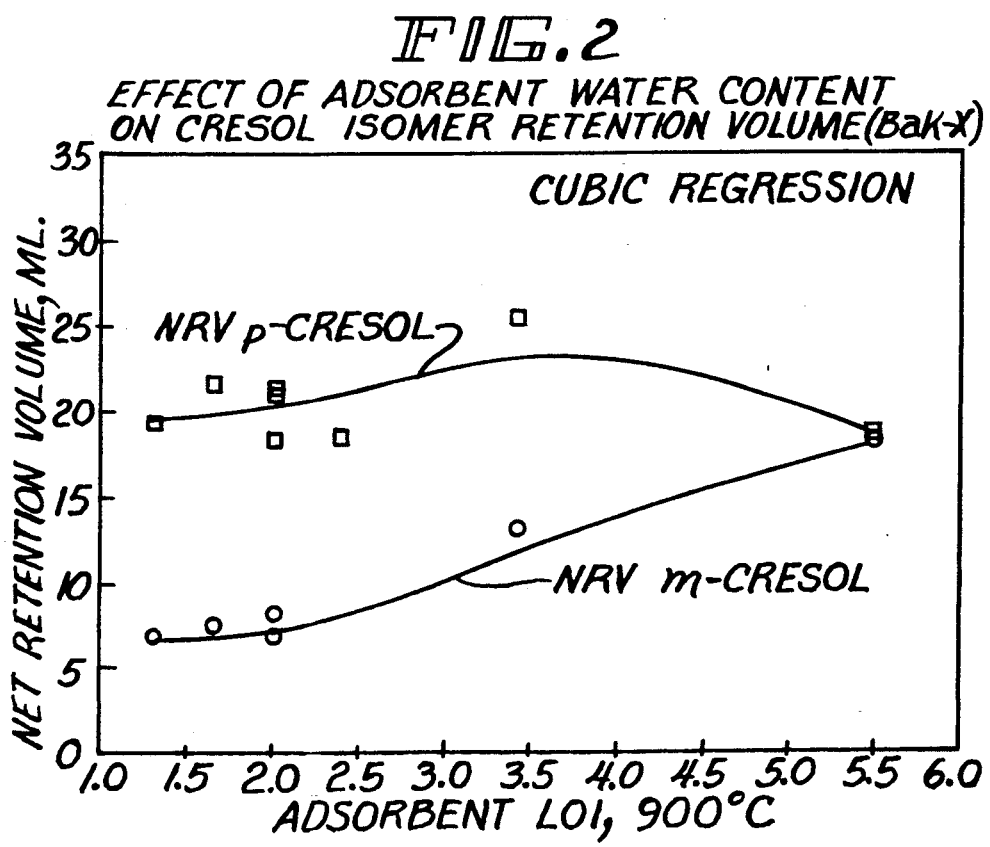
FIG. 2 is a summary of pulse test data obtained in the separation of Example I using Ba/K-X in which net retention volume is plotted vs. water content (LOI) of the adsorbent.

Several other pulse tests were conducted as described above except that the water content was varied. The results of all these pulse tests are shown in the graph of FIG. 2, wherein the net retention volumes of para-cresol and meta-cresol were plotted against the water content (LOI) of the adsorbent. As will be seen from FIG. 1 and the data points in FIG. 2, which have been connected by the lines drawn from a cubic spline fit, para-cresol and meta-cresol are virtually coextracted at an LOI of 5.48%. This is also evident from the selectivity factor of meta-cresol, in Table 2, of 1.005. This can be contrasted to the same separation where the adsorbent contains 3.42% of water (LOI) and the selectivity factor of meta-cresol to para-cresol is 1.94. In the latter case, the selectivity of ortho-cresol is so close to that of meta-cresol that meta-cresol could not be coextracted with para-cresol.

EXAMPLE II

The pulse test of Example I was repeated except that a 77 cc column of Ba-X, dried to a water content of 5.66% (LOI at 900° C.), was used as the adsorbent. The feed was 2 cc of a solution containing 0.5 cc each of o-cresol, m-cresol, and p-cresol, 0.3 cc of n-$C_{16}$ (tracer), and 2 cc of the desorbent, 1-pentanol. The temperature was 100° C. and the flow rate was 1.26 cc/min. The results are shown in FIG. 3 and set forth in the following Table 3.

TABLE 3

| Component | Gross Retention Volume | Net Retention Volume | Peak Width At Half Height | Selectivity Factor $\beta$ |
|---|---|---|---|---|
| n-$C_{16}$ | 48.0 | 0 | 14.3 | Tracer |
| p-Cresol | 65.1 | 17.1 | 23.6 | Ref. |
| m-Cresol | 65.6 | 17.6 | 23.5 | 0.97 |
| o-Cresol | 58.1 | 10.1 | 17.3 | 1.69 |

The results of several other pulse tests similar to the above tests, except at different water content of the adsorbent, Ba-X, are shown in FIG. 4. There it is noted that, at an LOI of 5.66%, the net retention volumes are virtually the same and hence no separation between the para- and meta-isomers takes place and are consequently coextracted. However, at 4.5% (LOI) water, there is substantial separation and, due to similar retention volumes for ortho-cresol and meta-cresol, meta- and para-cresol cannot be coextracted.

EXAMPLE III

The pulse test of Example I was repeated except that the adsorbent, Ba-X zeolite, was dried to a water content of 6.2% (LOI at 500° C.). The feed was 2.0 cc of a solution containing 2 g. each of o-cresol, m-cresol, p-cresol, 2,6-dimethyl phenol, o-ethyl phenol and 1.5 g. n-$C_{16}$. The temperature was 150° C. and the desorbent was 1-pentanol. The results are shown in the following Table 4.

TABLE 4

| Component | Gross Retention Volume (cc) | Net Retention Volume (cc) | Selectivity Factor ($\beta$) |
|---|---|---|---|
| n-$C_{16}$ | 41.9 | 0.0 | Tracer |
| 2,6-dimethyl phenol | 50.0 | 8.1 | 2.82 |
| o-ethyl phenol | 50.2 | 8.3 | 2.75 |
| o-cresol | 61.0 | 19.1 | 1.20 |
| p-cresol | 64.8 | 22.9 | Refer. |
| m-cresol | 65.2 | 23.3 | 0.98 |

In pilot plant runs, using the above adsorbent and desorbent, a commercial feedstock containing the above components was separated and an extract product containing p-cresol and m-cresol at 99.0–99.9% purity and 99.0–99.6% recovery was consistantly obtained.

I claim as my invention:

1. A process for coextracting para-cresol and meta-cresol from a feed mixture comprising para-cresol, ortho-cresol and meta-cresol and at least one other alkyl phenol comprising contacting said feed at adsorption conditions with an adsorbent comprising an X zeolite exchanged at ion exchangeable sites with barium ions or a mixture of barium and potassium ions, containing at least about 5 weight % water (LOI) to selectively adsorb said para-cresol and meta-cresol, contacting said adsorbent with a desorbent comprising an aliphatic alcohol, at desorption conditions, said adsorption and desorption conditions including a temperature within the range of from about 20° C. to about 250° C. and a pressure within the range of from about atmospheric to about 500 psig so as to maintain liquid phase.

2. The process of claim 1 wherein said feed is derived from coal tar, coal gasification, or a synthetic process.

3. The process of claim 1 wherein said feed mixture contains at least one other alkyl phenol selected from the group consisting of m-ethyl phenol, o-ethyl phenol, p-ethyl phenol, dimethyl phenols, diethyl phenols, methylethyl phenols and isopropyl phenols.

4. The process of claim 1 wherein said aliphatic alcohol has from 5 to 6 carbon atoms per molecule.

5. The process of claim 1 wherein said extract is contacted with a second adsorbent comprising an X or Y zeolite exchanged with barium, potassium, or barium and potassium ions, containing less than about 4 weight % water, for said para-cresol to selectively adsorb said para-cresol, contacting said adsorbent with a second desorbent, comprising an aliphatic alcohol or a mixture thereof with an aliphatic ketone at desorption conditions, said adsorption and desorption conditions including a temperature within the range of from about 20° C. to about 250° C. and a pressure within the range of from about atmospheric to about 500 psig so as to maintain liquid phase, eluting purified meta-cresol and thereafter recovering purified para-cresol.

6. The process of claim 5 wherein said second adsorbent contains about 2% (wt.) water.

* * * * *